United States Patent
Fridman et al.

(10) Patent No.: US 11,420,187 B2
(45) Date of Patent: Aug. 23, 2022

(54) CHROMIUM-ON-ALUMINA DEHYDROGENATION CATALYSTS AND METHODS FOR PREPARING AND USING THEM

(71) Applicant: Clariant International Ltd, Muttenz (CH)

(72) Inventors: Vladimir Z. Fridman, Louisville, KY (US); Adam Monroe, Louisville, KY (US)

(73) Assignee: CLARIANT INTERNATIONAL LTD, Muttenz (CH)

( * ) Notice: Subject to any disclaimer, the term of this patent is extended or adjusted under 35 U.S.C. 154(b) by 303 days.

(21) Appl. No.: 16/672,799

(22) Filed: Nov. 4, 2019

(65) Prior Publication Data

US 2020/0147588 A1 May 14, 2020

Related U.S. Application Data

(60) Provisional application No. 62/760,304, filed on Nov. 13, 2018.

(51) Int. Cl.

| | |
|---|---|
| *B01J 21/04* | (2006.01) |
| *B01J 23/26* | (2006.01) |
| *B01J 37/02* | (2006.01) |
| *B01J 35/10* | (2006.01) |
| *C07C 5/32* | (2006.01) |
| *B01J 37/08* | (2006.01) |
| *B01J 35/00* | (2006.01) |

(52) U.S. Cl.
CPC .............. *B01J 23/26* (2013.01); *B01J 21/04* (2013.01); *B01J 35/002* (2013.01); *B01J 35/1014* (2013.01); *B01J 35/1019* (2013.01); *B01J 37/0203* (2013.01); *B01J 37/086* (2013.01); *C07C 5/324* (2013.01)

(58) Field of Classification Search
None
See application file for complete search history.

(56) References Cited

U.S. PATENT DOCUMENTS

| | | | | |
|---|---|---|---|---|
| 2,271,356 | A | * | 1/1942 | Turkevich ............... C07C 5/322 208/134 |
| 3,784,669 | A | | 1/1974 | Elges, III |
| 4,321,149 | A | | 3/1982 | Hawxhurst |
| 4,369,295 | A | * | 1/1983 | McDaniel ............... C08F 10/00 526/348.2 |
| 4,560,546 | A | | 12/1985 | Perrone |
| 5,285,000 | A | | 2/1994 | Schwitzgebel |
| 5,951,457 | A | | 9/1999 | James |
| 8,835,347 | B2 | | 9/2014 | Ruettinger |
| 10,646,853 | B2 | | 5/2020 | Fridman |
| 2019/0308172 | A1 | | 10/2019 | Zou |

OTHER PUBLICATIONS

Machine translatin of Zhou (CN 107486195), publication date Dec. 19, 2017.*
Pan et al., Facile synthesis of highly ordered mesoporous chromium-alumina catalysts with improved catalytic activity and stability,J. Mater. Res., vol. 29, No. 6, Mar. 28, 2014.*
Kathy S. Collins, "A Practical Method of Neutralizing Cr(VI) in Phillips Polymerization Catalysts" ACS Symposium Series, Jan. 1, 2014.

\* cited by examiner

*Primary Examiner* — Jun Li

(57) ABSTRACT

The present disclosure relates to chromium-on-alumina dehydrogenation catalyst materials, to methods for making such catalysts, and to methods for dehydrogenating hydrocarbons using such catalysts. In one aspect, the disclosure provides a method for preparing a dehydrogenation catalyst material, the method comprising impregnating a chromium-on-alumina material with ascorbic acid, one or more of sodium, lithium and potassium (e.g., sodium), and chromium; and calcining the impregnated material to provide the dehydrogenation catalyst material comprising chromium in the range of 2.5 wt. % to about 35 wt. % and having no more than 100 ppm chromium(VI).

14 Claims, No Drawings

CHROMIUM-ON-ALUMINA DEHYDROGENATION CATALYSTS AND METHODS FOR PREPARING AND USING THEM

CROSS-REFERENCE TO RELATED APPLICATIONS

This application claims priority to U.S. Provisional Patent Application Ser. No. 62/760,304 filed Nov. 13, 2018, which is incorporated herein by reference in its entirety.

BACKGROUND OF THE DISCLOSURE

Field of the Disclosure

This disclosure relates generally to dehydrogenation catalyst materials and methods for preparing and using them. More particularly, the present disclosure relates to chromium-on-alumina dehydrogenation catalyst materials, to methods for making such catalysts, and to methods for dehydrogenating hydrocarbons using such catalysts.

Technical Background

Chromium-on-alumina catalysts are useful in a number of processes, such as alkane dehydrogenation. Alkane dehydrogenation is a recognized process for production of a variety of useful hydrocarbon products, such as in the dehydrogenation of propane to make propene for use in the polymer industry, dehydrogenations of n-butane to produce n-butene or alkylate and butadiene useful in tire production, and the dehydrogenation of isobutane to make isobutylene suitable for conversion to methyl tert-butyl ether, isooctane, and alkylates to supplement and enrich gasolines. Chromium-on-alumina dehydrogenation catalysts have a number of attractive features that provide for efficient, selective dehydrogenation processes.

Chromium-on-alumina catalysts typically contain chromium substantially in the Cr(III) oxidation state (for example, as $Cr_2O_3$) on an alumina surface. However, there generally remains some Cr(VI), which is carcinogenic and thus presents health risks, especially during catalyst handling. Current methods for the production of chromium-aluminum catalysts result in the presence of a small but significant amount of Cr(VI) in the final product. And while catalysts that do not include chromium (and thus do not include Cr(VI)) do exist, they are expensive, inefficient and/or ineffective.

Accordingly, there remains a need for a simple, cost-effective method for preparing a chromium-aluminum dehydrogenation catalyst material having a low or even undetectable amount of Cr(VI).

SUMMARY OF THE DISCLOSURE

In one aspect, the disclosure provides a method for preparing a dehydrogenation catalyst material, the method comprising
providing a porous chromium-on-alumina material;
impregnating the chromium-on-alumina material with ascorbic acid, one or more of sodium, lithium and potassium (e.g., sodium), and chromium; and
calcining the impregnated material to provide the dehydrogenation catalyst material having chromium in the range of 2.5-35 wt. % and having no more than 100 ppm chromium (VI).

In another aspect, the disclosure provides a method for preparing a dehydrogenation catalyst material, the method comprising
providing a porous chromium-on-alumina material;
impregnating the chromium-on-alumina material with ascorbic acid and chromium; and
calcining the impregnated material to provide the dehydrogenation catalyst material having chromium in the range of 2.5-35 wt. % and having no more than 100 ppm chromium (VI).

In another aspect, the disclosure provides a dehydrogenation catalyst having chromium in the range of 2.5 wt. % to about 35 wt. %, calculated as $Cr_2O_3$, disposed on an alumina support, and having no more than 100 ppm Cr(IV) on an elemental mass basis. The dehydrogenation catalyst can further include one or more alkali metals such as sodium, potassium or lithium (e.g., sodium). The dehydrogenation catalyst can also or alternatively include one or more alkali earth metals such as magnesium, calcium and barium, and/or one or more of cerium, zirconium and lanthanum.

Other aspects of the disclosure will be apparent to the person of ordinary skill in the art in view of the disclosure herein.

DETAILED DESCRIPTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within the degree of precision typical in the art.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The disclosure relates to dehydrogenation catalyst materials prepared by impregnating a chromium-on-alumina material with an aqueous impregnation solution that includes ascorbic acid, and calcining the impregnated material. The disclosure demonstrates that the amount of Cr(VI) present in the dehydrogenation catalyst material may advantageously be reduced as compared to the chromium-on-alumina catalyst material before the ascorbic acid impregnating step. The disclosure further demonstrates that such catalysts can exhibit performance comparable to or even better than conventional, commercially available dehydrogenation catalysts, while advantageously having a very low (or even undetectable) amount of Cr(VI).

Accordingly, one aspect of the disclosure is a method for preparing a dehydrogenation catalyst suitable, for example, for industrial-scale dehydrogenation reactions. The method includes providing a porous chromium-on-alumina material; impregnating the chromium-on-alumina material with ascorbic acid, one or more of sodium, lithium and potassium, and chromium, and calcining the impregnated material to provide the dehydrogenation catalyst having chromium in the range of about 2.5 wt. % to about 35 wt. %, calculated as $Cr_2O_3$, and having no more than 100 ppm Cr(VI), calculated on an elemental mass basis.

The chromium-on-alumina material before the impregnating step comprises alumina (i.e., aluminum oxide). As used herein, the term "oxide," including, e.g., "aluminum oxide" (i.e., alumina), "chromium oxide," etc., includes oxides in all forms and crystalline phases. For example, "aluminum oxide" includes $Al_2O_3$, $Al_2O_x$ wherein x is within the range of 1 to 3, etc. Unless otherwise indicated, regardless of the actual stoichiometry of the oxide, oxides are calculated as the most stable oxide for purposes of weight percent determinations. For example, the person of ordinary skill in the art will appreciate that a non-stoichiometric oxide of aluminum, or even another form of aluminum, may still be calculated as $Al_2O_3$.

The porous chromium-on-alumina material can be provided using conventional methods, e.g., by impregnation with a solution containing chromium followed by calcining. The porous chromium-on-alumina material can include other metallic species, e.g., as co-catalysts or promoters. The person of ordinary skill in the art will appreciate that porous chromium-on-alumina material before the impregnating step may itself be a catalytic material, such as, for example, a conventional alumina-supported chromium dehydrogenation catalyst. Advantageously, the present inventors have determined that, in certain such embodiments, the methods as otherwise described herein can provide a catalyst material having a reduced level of Cr(VI) that exhibits performance comparable to or even better than the chromium-on-alumina material before the impregnating step.

In certain embodiments of the methods as otherwise described herein, the porous chromium-on-alumina material before the impregnating step comprises at least about 50 wt. % alumina. For example, in certain embodiments of the methods as otherwise described herein, the chromium-on-alumina material before the impregnating step comprises at least about 55 wt. %, or about at least about 60 wt. %, or at least about 65 wt. %, or at least about 70 wt. %, or at least about 75 wt. %, or at least about 80 wt. %, or at least about 85 wt. %, or at least about 90 wt. %, or at least about 95 wt. %, or at least 97.5 wt. % alumina, calculated as $Al_2O_3$.

In certain embodiments of the methods as otherwise described herein, chromium is present in the porous chromium-on-alumina material before the impregnating step in an amount within the range of about 2.5 wt. % to about 35 wt. %, calculated as $Cr_2O_3$. For example, in certain embodiments of the methods as otherwise described herein, chromium is present in the chromium-on-alumina material before the impregnating step in an amount within the range of about 5 wt. % to about 35 wt. %, or about 10 wt. % to about 35 wt. %, or about 15 wt. % to about 35 wt. %, or about 20 wt. % to about 35 wt. %, or about 25 wt. % to about 35 wt. %, or about 2.5 wt. % to about 30 wt. %, or about 2.5 wt. % to about 25 wt. %, or about 2.5 wt. % to about 20 wt. %, or about 2.5 wt. % to about 15 wt. %, or about 5 wt. % to about 30 wt. %, or about 10 wt. % to about 25 wt. %, calculated as $Cr_2O_3$.

Conventional methods for providing chromium-on-alumina materials typically leave an undesirably high amount of Cr(VI) in the material. In certain embodiments of the methods as otherwise described herein, the chromium-on-alumina material before the ascorbic acid impregnating step comprises at least about 100 ppm Cr(VI) (i.e., calculated on an elemental mass basis). For example, in certain such embodiments, the chromium-on-alumina material before the ascorbic acid impregnating step comprises at least about 250 ppm, or at least about 300 ppm, or at least about 400 ppm, or at least about 500 ppm, or at least about 750 ppm, or at least about 1,000 ppm, or at least about 1,250 ppm, or at least about 1,500 ppm, or at least about 1,750 ppm, or at least about 2,000 ppm, or at least about 5,000 ppm, or at least 7,500 ppm, or at least 10,000 ppm, or at least 12,500 ppm, or at least 15,000 ppm, or at least 17,500 ppm, or at least 20,000 ppm chromium(VI) on an elemental mass basis. For example, in certain embodiments, the chromium-on-alumina material includes in the range of 1000-50,000 ppm, or 5000-50,000 ppm, or 10,000-50,000 ppm chromium (VI) before the ascorbic acid impregnating step.

The person of ordinary skill in the art will perform the impregnation in one or more impregnation steps based on the disclosure herein, e.g., from one or more aqueous solutions. Ascorbic acid can be provided using ascorbic acid and/or another ascorbate species, e.g., chromium ascorbate. An alkali metal such as sodium, lithium and/or potassium (e.g., sodium) can in certain embodiments be provided, for example, as the corresponding hydroxide. Chromium can be provided, for example, as chromium ascorbate.

In certain embodiments of the methods as otherwise described herein, the impregnation is performed by impregnating the chromium-on-alumina material with an aqueous impregnation solution comprising ascorbic acid present in an amount within the range of about 1 wt. % to about 30 wt. %; sodium, lithium and/or potassium, present in an amount within the range of about 0.1 wt. % to about 5 wt. % calculated on an oxide basis, and chromium, present in an amount within the range of about 0.1 wt. % to about 5 wt. % calculated as $Cr_2O_3$.

As noted above, in certain embodiments as otherwise described herein, the aqueous impregnation solution includes about 1 wt. % to about 30 wt. % of ascorbic acid. As used herein, "ascorbic acid" refers to ascorbic acid together with any other ascorbate species, with the amount determined as ascorbic acid. In certain embodiments of the methods as otherwise described herein, the ascorbic acid is present in the aqueous impregnation solution in an amount within the range of about 5 wt. % to about 25 wt. %. For example, in various embodiments of the methods as otherwise described herein, the ascorbic acid is present in the aqueous impregnation solution in an amount within the range of about 1 wt. % to about 30 wt. %, or about 5 wt. % to about 30 wt. %, or about 10 wt. % to about 30 wt. %, or about 12.5 wt. % to about 30 wt. %, or about 15 wt. % to about 30 wt. %, or about 20 wt. % to about 30 wt. %, or about 1 wt. % to about 25 wt. %, or about 5 wt. % to about 25 wt. %, or about 10 wt. % to about 25 wt. %, or about 12.5 wt. % to about 25 wt. %, or about 15 wt. % to about 25 wt. %, or about 1 wt. % to about 22.5 wt. %, or about 5 wt. % to about 22.5 wt. %, or about 10 wt. % to about 22.5 wt. %, or about 12.5 wt. % to about 22.5 wt. %, or about 15 wt. % to about 22.5 wt. %, or about 1 wt. % to about 20 wt. %, or about 5 wt. % to about 20 wt. %, or about 10 wt. % to about 20 wt. %, or about 12.5 wt. % to about 20 wt. %, or about 15 wt. % to about 20 wt. %, or about 1 wt. % to about 17.5 wt. %, or about 5 wt. % to about 17.5 wt. %, or about 10 wt. % to about 17.5 wt. %, or about 12.5 wt. % to about 17.5 wt. %.

As described above, in certain embodiments, the chromium-on-alumina material is impregnated with one or more of sodium, lithium and potassium. In certain such embodiments, the material is impregnated with sodium. Hydroxide base can in some embodiments be used to provide the sodium, lithium and/or potassium. Of course, other salts can be used. Accordingly, in certain embodiments of the methods as otherwise described herein, the aqueous impregnation solution further comprises sodium, lithium and/or potassium. For example, in certain embodiments of the methods as otherwise described herein, the aqueous impregnation solution comprises a sodium, lithium and/or potassium salt (e.g., a sodium salt). In certain such embodiments, the salt is a hydroxide or an ascorbate (e.g., sodium hydroxide or sodium ascorbate). In certain embodiments of the methods as otherwise described herein, sodium, lithium and/or potassium (e.g., sodium) is present in the aqueous impregnation solution in an amount within the range of about 0.1 wt. % to about 5 wt. %, or about 0.25 wt. % to about 5 wt. %, or about 0.5 wt. % to about 5 wt. %, or about 0.75 wt. % to about 5 wt. %, or about 1 wt. % to about 5 wt. %, or about 1.25 wt.

% to about 5 wt. %, or about 1.5 wt. % to about 5 wt. %, or about 1.75 wt. % to about 5 wt. %, or about 2 wt. % to about 5 wt. %, or about 2.5 wt. % to about 5 wt. %, or about 3 wt. % to about 5 wt. %, or about 3.5 wt. % to about 5 wt. %, or about 4 wt. % to about 5 wt. %, or about 0.1 wt. % to about 4.5 wt. %, or about 0.1 wt. % to about 4 wt. %, or about 0.1 wt. % to about 3.5 wt. %, or about 0.1 wt. % to about 3 wt. %, or about 0.1 wt. % to about 2.5 wt. %, or about 0.1 wt. % to about 2.25 wt. %, or about 0.1 wt. % to about 2 wt. %, or about 0.1 wt. % to about 1.75 wt. %, or about 0.1 wt. % to about 1.5 wt. %, or about 0.1 wt. % to about 1.25 wt. %, or about 0.1 wt. % to about 1 wt. %, or about 0.1 wt. % to about 0.75 wt. %, or about 0.1 wt. % to about 0.5 wt. %, or about 0.1 wt. % to about 0.25 wt. %, or about 0.25 wt. % to about 2 wt. %, or about 0.25 wt. % to about 1.5 wt. %, or about 0.5 wt. % to about 1 wt. %, calculated as oxide.

In certain embodiments of the methods as otherwise described herein, the aqueous impregnation solution further comprises chromium. For example, in certain embodiments of the methods as otherwise described herein, the aqueous impregnation solution comprises a chromium salt (e.g., ascorbate, acetate, or nitrate). In certain such embodiments, the chromium salt is chromium ascorbate. In certain embodiments of the methods as otherwise described herein, chromium is present in the aqueous impregnation solution in an amount within the range of about 0.01 wt. % to about 5 wt. %, or about 0.05 wt. % to about 5 wt. %, or about 0.1 wt. % to about 5 wt. %, or about 0.25 wt. % to about 5 wt. %, or about 0.5 wt. % to about 5 wt. %, or about 0.75 wt. % to about 5 wt. %, or about 1 wt. % to about 5 wt. %, or about 1.5 wt. % to about 5 wt. %, or about 2 wt. % to about 5 wt. %, or about 2.5 wt. % to about 5 wt. %, or about 3 wt. % to about 5 wt. %, or about 3.5 wt. % to about 5 wt. %, or about 4 wt. % to about 5 wt. %, or about 0.01 wt. % to about 4.5 wt. %, or about 0.01 wt. % to about 4 wt. %, or about 0.01 wt. % to about 3.5 wt. %, or about 0.01 wt. % to about 3 wt. %, or about 0.01 wt. % to about 2.5 wt. %, or about 0.01 wt. % to about 2 wt. %, or about 0.01 wt. % to about 1.5 wt. %, or about 0.01 wt. % to about 1 wt. %, or about 0.01 wt. % to about 0.75 wt. %, or about 0.01 wt. % to about 0.5 wt. %, or about 0.05 wt. % to about 4.5 wt. %, or about 0.05 wt. % to about 4 wt. %, or about 0.05 wt. % to about 3.5 wt. %, or about 0.05 wt. % to about 3 wt. %, or about 0.075 wt. % to about 2.5 wt. %, or about 0.1 wt. % to about 2 wt. %, or about 0.5 wt. % to about 1 wt. %, calculated as $Cr_2O_3$.

The amounts of various components described above can be combined in any suitable combination. For example, in certain embodiments of the methods as otherwise described herein, the ascorbic acid is present in the aqueous impregnation solution in an amount within the range of about 5 wt. % to about 15 wt. %, or about 5 wt. % to about 10 wt. %, or about 7.5 wt. % to about 12.5 wt. %, or about 10 wt. % to about 15 wt. %, sodium is present in the aqueous impregnation solution in an amount within the range of about 0.1 wt. % to about 1 wt. %, or about 0.1 wt. % to about 0.5 wt. %, or about 0.25 wt. % to about 0.75 wt. %, or about 0.5 wt. % to about 1 wt. %, and chromium is present in the aqueous impregnation solution in an amount within the range of about 0.1 wt. % to about 1 wt. %, or about 0.1 wt. % to about 0.5 wt. %, or about 0.25 wt. % to about 0.75 wt. %, or about 0.5 wt. % to about 1 wt. %. In certain such embodiments, the sodium is provided as sodium hydroxide or sodium ascorbate. In certain such embodiments, the chromium is provided as chromium ascorbate. In certain such embodiments, the chromium-on-alumina material before the impregnating step comprises at least about 50 wt. % alumina. In certain such embodiments, the chromium-on-alumina material before the impregnating step comprises at least about 100 ppm chromium(VI) on a molar basis.

In another example, in certain embodiments of the methods as otherwise described herein, the ascorbic acid is present in the aqueous impregnation solution in an amount within the range of about 5 wt. % to about 20 wt. %, for example, about 5 wt % to about 15 wt %, about 10 wt % to about 20 wt %, or about or about 10 wt. % to about 15 wt. %, or about 12.5 wt. % to about 17.5 wt. %, or about 15 wt. % to about 20 wt. %, sodium is present in the aqueous impregnation solution in an amount within the range of about 0.5 wt. % to about 1.5 wt. %, or about 0.5 wt. % to about 1 wt. %, or about 0.75 wt. % to about 1.25 wt. %, or about 1 wt. % to about 1.5 wt. %, and chromium is present in the aqueous impregnation solution in an amount within the range of about 1 wt. % to about 2 wt. %, or about 1 wt. % to about 1.5 wt. %, or about 1.25 wt. % to about 1.75 wt. %, or about 1.5 wt. % to about 2 wt. %. In certain such embodiments, the sodium is provided as sodium hydroxide or sodium ascorbate. In certain such embodiments, the chromium is provided as chromium ascorbate. In certain such embodiments, the chromium-on-alumina material before the impregnating step comprises at least about 50 wt. % alumina. In certain such embodiments, the chromium-on-alumina material before the impregnating step comprises at least about 100 ppm chromium(VI) on a molar basis.

In certain embodiments of the methods as otherwise described herein, the chromium-on-alumina material is impregnated with the aqueous impregnation solution at a temperature within the range of about 15° C. to about 50° C. For example, in certain embodiments of the methods as otherwise described herein, the chromium-on-alumina material is impregnated with the aqueous impregnation solution at a temperature within the range of about 20° C. to about 50° C., or about 25° C. to about 50° C., or about 30° C. to about 50° C., or about 35° C. to about 50° C., or about 15° C. to about 45° C., or about 15° C. to about 40° C., or about 15° C. to about 35° C., or about 15° C. to about 30° C., or about 20° C. to about 45° C., or about 25° C. to about 40° C.

In certain embodiments of the methods as otherwise described herein, the impregnating step is carried out over a period of time within the range of about 1 min. to about 4 hr., or about 1 min. to about 3.5 hr., or about 1 min. to about 3 hr., or about 1 min. to about 2.5 hr., or about 1 min. to about 2 hr., or about 1 min. to about 1.5 hr., or about 1 min. to about 1 hr., or about 2 min. to about 4 hr., or about 3 min. to about 4 hr., or about 5 min. to about 4 hr., or about 15 min. to about 4 hr., or about 0.5 hr. to about 4 hr., or about 1 hr. to about 4 hr., or about 1.5 hr. to about 4 hr., or about 2 hr. to about 4 hr., or about 2.5 hr. to about 4 hr., or about 3 hr. to about 4 hr., or about 2 min. to about 3.5 hr., or about 3 min. to about 3 hr., or about 5 min. to about 2.5 hr., or about 10 min. to about 2 hr., or about 15 min. to about 1.5 hr.

In certain embodiments of the methods as otherwise described herein, the chromium-on-alumina material after the impregnating step is calcined at a temperature within the range of about 100° C. to about 600° C. For example, in certain embodiments of the methods as otherwise described herein, the impregnated material is calcined at a temperature within the range of about 150° C. to about 600° C., or about 200° C. to about 600° C., or about 250° C. to about 600° C., or about 300° C. to about 600° C., or about 350° C. to about 600° C., or about 400° C. to about 600° C., or about 100° C. to about 550° C., or about 100° C. to about 500° C., or about 100° C. to about 450° C., or about 100° C. to about 400° C., or about 100° C. to about 350° C., or about 100° C. to about 300° C., or about 150° C. to about 550° C., or about 200° C. to about 550° C., or about 250° C. to about 500° C., or about 300° C. to about 500° C.

In certain embodiments of the methods as otherwise described herein, the chromium-on-alumina material after the impregnating step is calcined in an atmosphere comprising one or more of $N_2$, $O_2$ and $H_2O$. For example, in certain embodiments, the oxygen concentration of the calcining atmosphere is up to about 21 vol. %, the water concentration is up to about 100 vol. %, and/or the nitrogen concentration is up to 100 vol. %.

in certain embodiments of the methods as otherwise described herein, the impregnated material is calcined in an atmosphere comprising about 75 vol. % to 100 vol. %, or about 92.5 vol. % to about 99.75 vol. %, or about 95 vol. % to about 99.5 vol. % of $H_2O$. In certain such embodiments, the atmosphere further comprises up to about 5 vol. %, or about 0.075 vol. % to about 4 vol. %, or about 0.1 vol. % to about 3 vol. %, or about 0.125 vol. % to about 2 vol. %, or about 0.15 vol. % to about 1 vol. % of $O_2$. In certain such embodiments, the atmosphere further comprises up to about 20 vol. %, or about 0.1 vol. % to about 15 vol. %, or about 0.15 vol. % to about 10 vol. %, or about 0.2 vol. % to about 7.5 vol. %, or about 0.25 vol. % to about 5 vol. % of $N_2$.

In another example, in certain embodiments of the methods as otherwise described herein, the impregnated material is calcined in an atmosphere comprising about 90 vol. % to about 99 vol. %, or about 91 vol. % to about 98 vol. %, or about 92 vol. % to about 97 vol. % of $N_2$. In certain such embodiments, the atmosphere further comprises up to about 5 vol. %, or about 0.075 vol. % to about 4 vol. %, or about 0.1 vol. % to about 3 vol. %, or about 0.125 vol. % to about 2 vol. %, or about 0.15 vol. % to about 1 vol. % of $O_2$. In certain such embodiments, the atmosphere further comprises up to about 10 vol. %, or about 2 vol. % to about 9 vol. %, or about 3 vol. % to about 8 vol. %, or about 4 vol. % to about 7 vol. % of $H_2O$.

In certain embodiments of the methods as otherwise described herein, the impregnated material is calcined for a period of time within the range of about 5 min. to about 12 hr. For example, in certain embodiments of the methods as otherwise described herein, the impregnated material is calcined for a period of time within the range of about 10 min. to about 12 hr., or about 15 min. to about 12 hr., or about 20 min. to about 12 hr., or about 30 min. to about 12 hr., or about 45 min. to about 12 hr., or about 1 hr. to about 12 hr., or about 1.5 hr. to about 12 hr., or about 2 hr. to about 12 hr., or about 5 min. to about 11 hr., or about 5 min. to about 10 hr., or about 5 min. to about 9 hr., or about 5 min. to about 8 hr., or about 5 min. to about 7.5 hr., or about 5 min. to about 7 hr., or about 5 min. to about 6.5 hr., or about 5 min. to about 6 hr., or about 5 min. to about 5.5 hr., or about 5 min. to about 5 hr., or about 30 min. to about 11 hr., or about 1 hr. to about 10 hr., or about 1.5 hr. to about 9 hr., or about 2 hr. to about 8 hr.

Notably, the methods described herein can be performed to provide chromium-on-alumina dehydrogenation catalyst materials with greatly reduced amounts of Cr(VI). For example, in certain embodiments, the impregnation and calcination are performed to provide the dehydrogenation catalyst material with no more than 100 ppm chromium(VI). In certain such embodiments, the impregnation and calcination are performed to provide the dehydrogenation catalyst material with no more than 50 ppm chromium(VI), no more than 20 ppm Cr(VI), or even no more than 10 ppm Cr(VI). In certain embodiments as otherwise described herein, the impregnation and calcining are performed to reduce the amount of Cr(VI) by at least 99% (i.e., comparing the amount of Cr(VI) in the material as provided with the material after the impregnation and calcined).

Another aspect of the disclosure is a dehydrogenation catalyst having chromium in the range of about 2.5 wt. % to about 35 wt. % (e.g., about 5 wt. % to about 30 wt. %, or about 10 wt. % to about 25 wt. %, or about 10 wt % to about 30 wt %), calculated as $Cr_2O_3$, disposed on an alumina support, and having no more than 100 ppm Cr(IV). In certain such embodiments, the dehydrogenation catalyst includes no more than 50 ppm, no more than 20 ppm, or even no more than 10 ppm Cr(IV). Such dehydrogenation catalysts can be, for example, prepared by a method as described herein. Advantageously, the present inventors have determined that the use of catalyst materials described herein, which can be substantially free of Cr(VI) (e.g., less than about 100 ppm, less than about 50 ppm, or less than about 10 ppm Cr(VI) on a molar basis), can catalyze a hydrocarbon dehydrogenation reaction at an efficiency comparable to or better than conventional, commercially available catalyst materials (e.g., having substantially greater amounts of Cr(IV)).

Such dehydrogenation catalysts can in certain embodiments further include one or more alkali metals such as sodium, lithium and potassium (e.g., sodium).

Of course, the person of ordinary skill in the art will appreciate that the dehydrogenation catalysts described herein can include other metallic components. For example, in certain embodiments, a dehydrogenation catalyst as otherwise described herein includes one or more alkaline earth metals such as magnesium, calcium and barium. In certain such embodiments, the alkaline earth metal is magnesium. The alkaline earth metal(s) can be present in the final catalyst in a variety of total amounts, for example, in the range of 0.05 wt % to 5 wt % (or 0.1 wt % to 2 wt %, or 0.05 wt % to 1 wt %) calculated as oxide on an as-calcined basis.

Similarly, the dehydrogenation catalysts described herein can include zirconium. Zirconium can be present in the final catalyst in a variety of total amounts, for example, in the range of 0.05 wt % to 5 wt % (or 0.1 wt % to 2 wt %, or 0.05 wt % to 1 wt %) calculated as $ZrO_2$ on an as-calcined basis.

Similarly, the dehydrogenation catalysts described herein can include cerium and/or lanthanum. Cerium and/or lanthanum can be present in the final catalyst in a variety of total amounts, for example, in the range of 0.05 wt % to 5 wt % (or 0.1 wt % to 2 wt %, or 0.05 wt % to 1 wt %) calculated as trivalent oxide on an as-calcined basis.

In certain embodiments of the materials as otherwise described herein, the surface area of the catalyst material is at least about 60 m$^2$/g, or at least about 80 m$^2$/g, or at least about 100 m$^2$/g, or at least about 130 m$^2$/g, or at least about 150 m$^2$/g, or at least about 175 m$^2$/g.

In certain embodiments of the materials as otherwise described herein, Cr(III) is present in the catalyst material in an amount within the range of about 2.5 wt. % to about 35 wt. %, calculated as $Cr_2O_3$. For example, in certain embodiments of the materials as otherwise described herein, Cr(III) is present in the catalyst material in an amount within the range of about 5 wt. % to about 35 wt. %, or about 10 wt. % to about 35 wt. %, or about 15 wt. % to about 35 wt. %, or about 20 wt. % to about 35 wt. %, or about 25 wt. % to about 35 wt. %, or about 2.5 wt. % to about 30 wt. %, or about 2.5 wt. % to about 25 wt. %, or about 2.5 wt. % to about 20 wt. %, or about 2.5 wt. % to about 15 wt. %, or about 5 wt. % to about 30 wt. %, or about 10 wt. % to about 25 wt. %, calculated as $Cr_2O_3$. In certain such embodiments, the catalyst material further comprises at least about 50 wt. % alumina, calculated as $Al_2O_3$.

The materials described herein are especially useful in hydrocarbon dehydrogenation reactions. Accordingly, another aspect of the disclosure is a method for dehydrogenation alkanes that includes contacting a hydrocarbon feed with a catalyst material as otherwise described herein, under conditions sufficient to cause hydrocarbon dehydrogenation.

In certain embodiments of the dehydrogenation methods as otherwise described herein, the hydrocarbon feed comprises one or more $C_3$-$C_5$ alkanes. For example, in certain embodiments of the dehydrogenation methods as otherwise described herein, the hydrocarbon feed comprises propane.

The contacting of the feed with the catalyst materials described herein can be conducted in a variety of ways familiar to the person of ordinary skill in the art. Conventional equipment and processes can be used in conjunction with the catalyst materials of the disclosure to provide beneficial performance. Thus, the catalyst may be contained in one bed within a reactor vessel or divided up among a plurality of beds within a reactor. The reaction system may contain one or more reaction vessels in series. The feed to the reaction zone can flow vertically upwards, or downwards through the catalyst bed in a typical plug flow reactor, or horizontally across the catalyst bed in a radial flow type reactor.

The contacting of the feed with the catalyst material can be performed using conventional methods. For example, the feed may be introduced into the reaction zone containing the catalyst material at a constant rate, or alternatively, at a variable rate.

In certain embodiments of the dehydrogenation methods as otherwise described herein, the feed is contacted with the provided catalyst material at a liquid hourly space velocity (LHSV) within the range of about 0.25 $h^{-1}$ to about 4 $h^{-1}$. For example, in certain embodiments of the dehydrogenation methods as otherwise described herein, the feed is contacted with the provided catalyst composition at a liquid hourly space velocity of about 0.5 $h^{-1}$ to about 4 $h^{-1}$, or about 0.75 $h^{-1}$ to about 4 $h^{-1}$, or about 1 $h^{-1}$ to about 4 $h^{-1}$, or about 1.25 $h^{-1}$ to about 4 $h^{-1}$, or about 1.5 $h^{-1}$ to about 4 $h^{-1}$, or about 0.25 $h^{-1}$ to about 3.75 $h^{-1}$, or about 0.25 $h^{-1}$ to about 3.5 $h^{-1}$, or about 0.25 $h^{-1}$ to about 3.25 $h^{-1}$, or about 0.25 $h^{-1}$ to about 3 $h^{-1}$, or about 0.25 $h^{-1}$ to about 2.75 $h^{-1}$, or about 0.25 $h^{-1}$ to about 2.5 $h^{-1}$, or about 0.5 $h^{-1}$ to about 3.5 $h^{-1}$, or about 0.75 $h^{-1}$ to about 3 $h^{-1}$, or about 1 $h^{-1}$ to about 2.75 $h^{-1}$, or about 1.25 $h^{-1}$ to about 2.5 $h^{-1}$.

In certain embodiments of the dehydrogenation methods as otherwise described herein, the method is carried out at a temperature within the range of about 400° C. to about 750° C. For example, in certain embodiments of the dehydrogenation methods as otherwise described herein, the method is carried out at a temperature within the range of about 400° C. to about 700° C., or about 400° C. to about 650° C., or about 400° C. to about 600° C., or about 400° C. to about 550° C., or about 450° C. to about 750° C., or about 500° C. to about 750° C., or about 550° C. to about 750° C., or about 600° C. to about 750° C., or about 450° C. to about 700° C., or about 500° C. to about 650° C.

In certain embodiments of the dehydrogenation methods as otherwise described herein, the method is carried out at a pressure within the range of about 0.1 bar to about 1.5 bar. For example, in certain embodiments of the dehydrogenation methods as otherwise described herein, the methods is carried out at a pressure within the range of about 0.1 bar to about 1.25 bar, or about 0.1 bar to about 1 bar, or about 0.1 bar to about 0.75 bar, or about 0.1 bar to about 0.5 bar, or about 0.2 bar to about 1.5 bar, or about 0.3 bar to about 1.5 bar, or about 0.4 bar to about 1.5 bar, or about 0.5 bar to about 1.5 bar, or about 0.2 bar to about 1.25 bar, or about 0.3 bar to about 1 bar, or about 0.4 bar to about 0.75 bar.

EXAMPLES

The Examples that follow are illustrative of specific embodiments of the invention, and various uses thereof. They are set forth for explanatory purposes only, and are not to be taken as limiting the invention.

Example 1. Catalyst Preparation

A conventional chromium-on-alumina catalyst, C, comprising 20 wt. % chromium (calculated as $Cr_2O_3$) was prepared according to known methods.

The chromium-on-alumina material C was impregnated with an aqueous solution of 10 wt. % ascorbic acid, and calcined at 120° C. in an atmosphere of 80 vol. % $N_2$, 19.5 vol. % $O_2$, and 0.1 vol. % $H_2O$, to provide catalyst B1.

The chromium-on-alumina material C was impregnated with an aqueous solution of 10 wt. % ascorbic acid, 0.65 wt. % sodium (present as NaOH, calculated as $Na_2O$), and 0.2 wt. % chromium (present as chromium ascorbate, calculated as $Cr_2O_3$), and calcined at 315° C. in an atmosphere of 95 vol. % $N_2$, 0.2 vol. % $O_2$, and 4.8 vol. % $H_2O$, to provide catalyst A1.

The chromium-on-alumina material C was impregnated with an aqueous solution of 15 wt. % ascorbic acid, 1 wt. % sodium (present as NaOH, calculated as $Na_2O$), and 1.5 wt. % chromium (present as chromium ascorbate, calculated as $Cr_2O_3$), and calcined at 425° C. in an atmosphere of 0.5 vol. % $N_2$, 0.2 vol. % $O_2$, and 99.3 vol. % $H_2O$, to provide catalyst A2.

The chromium-on-alumina material C was impregnated with an aqueous solution of 15 wt. % ascorbic acid, 1 wt. % sodium (present as NaOH, calculated as $Na_2O$), and 1.5 wt. % chromium (present as chromium ascorbate, calculated as $Cr_2O_3$), and calcined at 450° C. in an atmosphere of 0.5 vol. % $N_2$, 0.2 vol. % $O_2$, and 99.3 vol. % $H_2O$, to provide catalyst A3.

TABLE 1

| Catalyst Properties | | | | | |
|---|---|---|---|---|---|
|  | C | B1 | A1 | A2 | A3 |
| Cr(VI) (ppm) | 11,000 | 2.2 | 3.9 | 2 | 6.5 |

Example 2. Propane Dehydrogenation

Catalyst materials prepared according to Example 1 were tested as prepared in a fixed-bed reactor. A feed containing 100 mol. % propane was passed over a catalyst bed at 2.0 $h^{-1}$ liquid hourly space velocity (LHSV), at a temperature within the range of 540-600° C. Results are provided in Table 2, below.

TABLE 2

| Property | C (wt. %) | B1 (wt. %) | A1 (wt. %) | A2 (wt. %) | A3 (wt. %) |
|---|---|---|---|---|---|
| Propane Dehydrogenation | | | | | |
| Loss on Ignition (1000° C.) | <0.01 | 5.2 | 5.3 | 4.98 | 4.1 |
| 1000° F. | | | | | |
| C1 to C2 | 2.22 | 3.32 | 2.2 | 1.89 | 2.31 |
| Propane Conversion | 32.09 | 33.25 | 31.06 | 34.23 | 31.06 |
| Propylene Selectivity | 83.06 | 77.77 | 83.67 | 83.89 | 82.63 |
| Propylene Yield | 26.62 | 25.8 | 25.91 | 28.69 | 25.57 |
| Coke Yield | 0.71 | 1.41 | 0.71 | 0.71 | 0.78 |
| 1050° F. | | | | | |
| C1 to C2 | 4.83 | 5.87 | 4.37 | 4.34 | 4.61 |
| Propane Conversion | 44.34 | 44.58 | 42.05 | 47.68 | 41.57 |
| Propylene Selectivity | 77.65 | 71.76 | 78.05 | 78.22 | 76.18 |
| Propylene Yield | 34.44 | 32.01 | 32.85 | 37.35 | 31.7 |
| Coke Yield | 1.1 | 2.77 | 1.09 | 1.41 | 1.25 |
| 1100° F. | | | | | |
| C1 to C2 | 9.13 | 9.62 | 8.47 | 9.14 | 9.44 |
| Propane Conversion | 57.44 | 58.01 | 54.69 | 60.59 | 54.49 |
| Propylene Selectivity | 70.02 | 62.74 | 69.3 | 68.38 | 66.07 |
| Propylene Yield | 40.22 | 36.39 | 37.86 | 41.43 | 35.97 |
| Coke Yield | 3.26 | 6.57 | 3.45 | 4.07 | 3.89 |

The results show that the performance of the catalysts, each having less than 10 ppm Cr(VI), was acceptable. Dehydrogenation results of catalyst materials A1-3 further demonstrate that inclusion of one or more of an alkali metal such as sodium, lithium, or potassium in the aqueous impregnation solution can provide increased propylene selectivity.

What is claimed is:

1. A method for preparing a dehydrogenation catalyst material, the method comprising
   providing a porous chromium-on-alumina material having at least 1000 ppm Cr(VI);
   impregnating the chromium-on-alumina material with an aqueous impregnating solution comprising ascorbic acid, one or more of sodium, lithium and potassium, and chromium; and
   calcining the impregnated material to provide the dehydrogenation catalyst material having chromium in the range of 10-35 2.5 wt. % and having no more than 100 ppm chromium(VI).

2. A method according to claim 1, wherein the chromium-on-alumina catalyst material before the impregnating step comprises at least 50 wt. % alumina, calculated as $Al_2O_3$.

3. A method according to claim 1, wherein chromium is present in the chromium-on-alumina catalyst material before the impregnating step in an amount within the range of about 2.5 wt. % to about 35 wt. %, calculated as $Cr_2O_3$.

4. A method according to claim 1, wherein the chromium-on-alumina catalyst material before the ascorbic acid impregnating step comprises at least about 5,000 ppm chromium(VI).

5. A method according to claim 1, wherein the impregnation is performed by impregnating the porous chromium-on-alumina material with an aqueous impregnation solution comprising
   ascorbic acid, present in an amount within the range of about 1 wt. % to about 30 wt. %,
   sodium, lithium and/or potassium, present in an amount within the range of about 0.1 wt. % to about 5 wt. % calculated on an oxide basis, and
   chromium, present in an amount within the range of about 0.01 wt. % to about 5 wt. % calculated as $Cr_2O_3$.

6. A method according to claim 5, wherein the ascorbic acid is present in the aqueous impregnation solution in an amount within the range of about 5 wt. % to about 25 wt. %.

7. A method according to claim 5, wherein chromium is present in the aqueous impregnation solution in an amount within the range of about 0.1 wt. % to about 5 wt. %, calculated as $Cr_2O_3$.

8. A method according to claim 7, wherein chromium is present in the aqueous impregnation solution in an amount within the range of 0.1 wt. % to 3 wt. %.

9. A method according to claim 1, wherein the impregnated material is calcined at a temperature within the range of 100° C. to 600° C.

10. A method according to claim 1, wherein the dehydrogenation catalyst material has no more than 20 ppm chromium(VI) on an elemental mass basis.

11. A method according to claim 1, wherein the dehydrogenation catalyst material has no more than 10 ppm chromium(VI) on an elemental mass basis.

12. A method according to claim 10, wherein the porous chromium-on-alumina material has at least 7500 ppm Cr(VI).

13. A method according to claim 11, wherein the porous chromium-on-alumina material has at least 7500 ppm Cr(VI).

14. A method according to claim 12, wherein the porous chromium-on-alumina material has 15-35 wt % chromium calculated as $Cr_2O_3$.

* * * * *